(12) United States Patent
Carter (10) Patent No.: US 7,179,838 B2
(45) Date of Patent: Feb. 20, 2007

(54) COUMARIN ANALOG COMPOUNDS FOR SAFER ANTICOAGULANT TREATMENT

(75) Inventor: Daniel C. Carter, Huntsville, AL (US)

(73) Assignee: New Century Pharmaceuticals, Inc., Huntsville, AL (US)

( * ) Notice: Subject to any disclaimer, the term of this patent is extended or adjusted under 35 U.S.C. 154(b) by 0 days.

(21) Appl. No.: 10/629,858

(22) Filed: Jul. 30, 2003

(65) Prior Publication Data

US 2004/0058985 A1    Mar. 25, 2004

Related U.S. Application Data

(60) Provisional application No. 60/399,126, filed on Jul. 30, 2002.

(51) Int. Cl.
*A61K 31/352*    (2006.01)
*C07D 311/52*    (2006.01)

(52) U.S. Cl. ...................................... 514/457; 549/286
(58) Field of Classification Search ................ 549/286; 514/457
See application file for complete search history.

(56) References Cited

U.S. PATENT DOCUMENTS 2,427,578 A * 9/1947 Stahmann et al. .......... 549/286

OTHER PUBLICATIONS

Roush et al, J. Org. Chem., vol. 52, p. 5127-5136 (1987).*
Ivanov et al, Arch. Pharm. (Weinheim), vol. 323, p. 521-522 (1990).*
Manolov et al, Eur. J. Med. Chem., vol. 30, p. 531-535 (1995).*

* cited by examiner

*Primary Examiner*—Bernard Dentz
(74) *Attorney, Agent, or Firm*—B. Aaron Schulman; Stites & Harbison PLLC (57) ABSTRACT

The present invention relates to the albumin-guided development of coumarin analogs and the analogs developed thereby. The coumarin analogs of the present invention are identified and isolated by the fact that they have binding sites to albumin which are different than the binding sites of conventional coumarin analogs such as sodium warfarin, and as a result will be less prone to be displaced since the binding site of sodium warfarin is shared by numerous drugs such as aspirin. The coumarin analogs of the invention are advantageous because they can achieve the effects of the prior coumarin analogs with a minimum of metabolic complications and undesirable side effects.

7 Claims, 6 Drawing Sheets

ALBUMIN NCP014 COMPLEX (IB)

DETAILS OF THE BINDING
WITHIN THE IB SITES

*FIG. 1*

ALBUMIN NCP014 COMPLEX (1IA)

DETAILS OF NCP014 BINDING
WITHIN THE I1A SITE

FIG. 2

ALBUMIN NCP014 COMPLEX (W/ MYRISTATE)

OVERALL BINDING OF
NCP014 ON HUMAN
SERUM ALBUMIN

FIG. 3

UNBIASED DIFFERENCE MAP (1B)

DIFFERENCE ELECTRON DENSITY (UNREFINED)
OF NCP014 IN SITE 1B

FIG. 4A

UNBIASED DIFFERENCE MAP (1A)

DIFFERENCE ELECTRON DENSITY (UNREFINED)
OF NCP014 IN SITE 1A

COUMARIN ANALOG COMPOUNDS FOR SAFER ANTICOAGULANT TREATMENT

CROSS-REFERENCE TO RELATED APPLICATIONS

This application claims the benefit of U.S. Provisional Application Ser. No. 60/399,126, filed Jul. 30, 2002.

FIELD OF THE INVENTION

The invention relates to the albumin-guided development of certain coumarin analog compounds which can be used as safer and more effective alternatives to previous analogs such as Sodium Warfarin, as well as methods for obtaining the coumarin analogs by assessing and utilizing the albumin-binding characteristics of the individual compounds so that the coumarin analogs of the invention may be identified or designed which will bind at sites which are less likely to be displaced by other drugs and which will thus result in safer, more controlled levels of coumarin analog in the bloodstream. Accordingly, the invention also relates to methods of providing anti-coagulant or anti-thrombotic treatment utilizing effective amounts of the coumarin analogs of the present invention which will have reduced potential for unfavorable drug interactions, reduced metabolic complications, and improved controllability within their therapeutic range.

BACKGROUND OF THE INVENTION

It has long been known to utilize coumarin analogs for various purposes such as to provide anti-thrombotic effects where needed. For example, one such analog known as Sodium Warfarin, which has been marketed under the tradename "Coumadin®" by the DuPont company, is considered the generally accepted standard in the field of coumarin analogs, although this drug has been marketed as a generic drug under other brand names such as Marevan; Prothromadin; Tintorane; Warfarin sodium; Warfilone; and Waran. Coumarin analogs such as sodium warfarin are disclosed, for example, in U.S. Pat. Nos. 2,427,578; 2,765,321; 5,591,403; and 6,512,005, incorporated herein by reference, and these compounds have been utilized primarily for the ability to provide localized anti-thrombotic effects as needed during therapeutic treatment.

However, such presently available coumarin analogs suffer from various drawbacks, including the fact that they may induce undesirable side effects. One example of undesirable effects relates to the extensive listing of unfavorable drug interactions for sodium warfarin, one in fact which is the most extensive among approved pharmaceuticals. Many of these unfavorable drug interactions arise because these analogs have been determined to bind serum albumin at a binding site common to many other drugs and compounds. This albumin binding site for many drugs is classically referred to as the Sudlow Site II. As a result, particularly in cases wherein a patient taking anti-coagulant drugs is taking a second medication at the same time, there is a great likelihood that the coumarin analog drug will be displaced from the serum albumin, resulting in the very dangerous situation where the analog will have an increased active concentration in the bloodstream which can result in serious metabolic consequences and other harmful conditions. Moreover, the useful life of the coumarin drug can be severely restricted and thus the patient may not be getting a sufficient supply of the blood-thinning drug which also may result in severe problems including blood clots, embolism, and even stroke.

Thus, although there have been numerous coumarin analogs synthesized and studied over the past several decades, none of these have been developed with a focus on the albumin protein binding characteristics of the various coumarin drugs that have been developed, and with the current heavy emphasis and expense in achieving product safety and efficacy, as well as regulatory approval, such an approach will be extremely helpful and cost effective in designing and selecting safe and effective coumarin alternatives earlier in the dug development process. It is thus needed in the field drug develop methods of obtaining coumarin alternatives using a focus which is structurally based on their protein binding properties, particularly the binding properties with serum albumin so as to best determine which analogs will bind to sites which have a far lesser likelihood of being displaced by other drugs or particular conditions in the bloodstream and which provide a stable and controlled reservoir of active drug in the blood stream.

SUMMARY OF THE INVENTION

It is thus an object of the present invention to develop coumarin analogs for use as pharmaceuticals which would directly mimic treatments for which Sodium Warfarin is used, yet which avoid the albumin binding sites of sodium warfarin so as to be safer and when bound to the albumin at favorable locations provides a stable and more controlled active drug in the bloodstream.

It is further an object of the present invention to utilize the atomic determination of serum albumin binding sites in the development of the coumarin analogs of the present invention, thus providing definitive information on each analog which can bind to alternative sites, producing lead compounds which are less likely to be displaced in the presence of competing drugs.

It is still further an object of the present invention to develop improved drugs which can be used in place of sodium warfarin with reduced drug interactions, reduced metabolic complications, and improved controllability within therapeutic ranges.

It is even further an object of the present invention to develop methods for identifying and isolating albumin-binding coumarin analogs which bind to alternative sites on the albumin and which are useful in therapeutic treatment methods, and the coumarin analogs identified and isolated thereby.

It is yet further an object of the invention to develop methods for administering an anti-coagulant agent in amounts effective to achieve a desired therapeutic anti-coagulant or anti-thrombotic effect by administering an effective amount of the alternative coumarin analogs developed in accordance with the present invention.

These and other objects are achieved by virtue of the present invention which provides novel coumarin analogs useful in treatments which currently use conventional sodium warfarin products such as Coumadin®, along with their enantiomeric forms, derivatives, and active metabolic products as well. The coumarin analogs of the present invention are advantageous in that they are selected by virtue of their affinity for binding sites on albumin other than the binding site common to sodium warfarin and the other forms of warfarin, a site which also forms the binding site for numerous other drugs and compounds. As a result, the coumarin analogs of the present invention will bind at sites which have high affinity for the analog, yet are far less likely to be displaced by other drugs because the alternative sites do not appear to have a large number of competing drugs or compounds that bind at those sites. The coumarin analogs of the present invention can thus provide the same effective anti-coagulant properties of the prior art warfarin compounds but are safer and more effective because of the greater likelihood that the analogs of the invention will be in stable equilibrium between albumin and the active free drug in the bloodstream and will not be as susceptible to drug displacement interactions which may result in dangerous, higher than desired effective dosing. The present invention also provides a method for identifying and isolating these novel and effective coumarin analogs by virtue of their ability to bind with alternative sites on albumin, or active albumin fragments, and provides methods of anti-coagulant therapy wherein an effective amount of the coumarin analog of the present invention is administered to a patient in need of such therapy.

These and other features of the present invention as set forth in, or will become obvious from, the detailed description of the preferred embodiments provided hereinbelow.

DETAILED DESCRIPTION OF THE PREFERRED EMBODIMENTS

In accordance with the present invention, a system for drug development is provided wherein coumarin analogs are identified and isolated by virtue of their unique and unusual binding sites on serum albumin relative to other coumarin based anti-coagulants. The term coumarin analog or coumarin compound refers to those compounds, enantiomers and derivatives of coumarin which are derived from coumarin and retain all of the biological activity of coumarin. By "anti-coagulant" or "anti-coagulant agent" means a coagulation inhibitory agent, or an agent that treats, inhibits or prevents blood coagulation. Such agents are commonly known and utilized when therapeutically or medically necessary and include such agents as warfarin and heparin. Other forms of warfarin anti-coagulant agents include crystalline warfarin, sodium warfarin or amorphous sodium warfarin. These compounds are highly potent anticoagulants and are generally administered orally and used extensively as active pharmaceutical ingredients (APIs) in amounts effective to achieve the level of anti-coagulation or anti-thrombosis as needed for a particular patient. Thus, as recognized by one skilled in the art, the effective amount of any such agent, including agents and compounds in accordance with the present invention as described further below, will be that amount which will achieve a desired effect, e.g., appropriate prevention of blood coagulation, for a particular patient depending on the size, gender and medical condition of the patient.

In accordance with the present invention, there is provided a method for identifying and isolating coumarin analogs which have improved properties which comprises obtaining candidate coumarin analogs which retain the anti-coagulant properties of coumarin and other analogs such as sodium warfarin, and introducing said coumarin analog to a serum albumin, such as human serum albumin or rat serum albumin, such that the binding characteristics of the candidate coumarin analog can be determined, including the specific binding site or subsite therein of the coumarin analog to albumin. By "serum albumin" is thus meant any serum albumin or active fragment thereof which will exhibit binding to a coumarin analog. Previously, conventional coumarin analogs such as sodium warfarin suffer from the drawback that they bind to serum albumin at a classical major site (in the IIA region) which is very common and which will also constitute the binding site for other drugs and compounds such as aspirin and numerous other drugs which may be administered along with an anti-coagulant or anti-thrombotic drug such as sodium warfarin. The problem is that when the second drug is administered to the patient, there is a great likelihood of drug displacement at the common IIA binding site where sodium warfarin and other similar analogs will bind to the serum albumin. As a result of this drug displacement, the prior art coumarin analogs have a far greater likelihood of being displaced and becoming free in the blood stream. This possibility presents severe potential damage to the patient in a number of ways. In particular, the elevated amount of free coumarin analog in the bloodstream can itself lead to a wide variety of metabolic and cardiovascular problems since this drug can have potentially drastic effects if not properly controlled. Even further, to the extent the coumarin drug in free form is eliminated more quickly from the bloodstream that would normally occur in the state wherein the analog was bound to albumin, the patient may not receive the anticoagulant effect desired by the use of the drug and may thus suffer the conditions that are intended to be avoided by the anticoagulant treatment, e.g., artery blockage, blood clots, embolism and stroke.

To the contrary, the present invention is designed to determine which coumarin analogs bind to site on serum albumin which are not the same as the site targeted by the commonly used coumarin alternatives, particularly sodium warfarin. By determining the albumin binding characteristics of potential candidate coumarin analogs, and then selecting those analogs which bind at a site other than the site as which coumarin analogs such as sodium warfarin will bind, an improved coumarin analog will be obtained that will suitably be bound with albumin at a different location than sodium warfarin, and such a coumarin analog will be far less likely to be displaced by other drugs, endogenous ligands or other conditions in the bloodstream, and will constitute a far safer and more effective compound for anti-coagulant treatment. Accordingly, in accordance with the present invention, an improved coumarin analog is obtained which will bind to an albumin binding site or region which will have altered affinity for the coumarin analog and which will be much less likely to be subject to drug displacement. The resulting coumarin analogs in accordance with the present invention will thus be more controllable than prior art coumarin alternatives, and can also be used with greater safely and efficacy with fewer side effects such as metabolic complications.

In accordance with the present invention, there are provided coumarin analog compounds, the parent compounds for which do not bind at the same albumin binding site as prior conventional coumarin analogs such as sodium warfarin. In particular, the following specific coumarin analog compounds, identified herein as NCP 014, 014a, 014b, 023, and 023a–h, have been identified, isolated or suggested in accordance with the present invention, and such compounds will maintain the ability to act as anticoagulant agents, but will not be subject to drug displacement in the same manner as conventional coumarin analogs such as sodium warfarin which bind to the subsite located in the IIA binding region of albumin:

NCP 014

NCP 014a

NCP 014b

NCP 023

NCP 023a

NCP 023b

NCP 023c

NCP 023d

NCP 023e

NCP 023f

Figure 1:
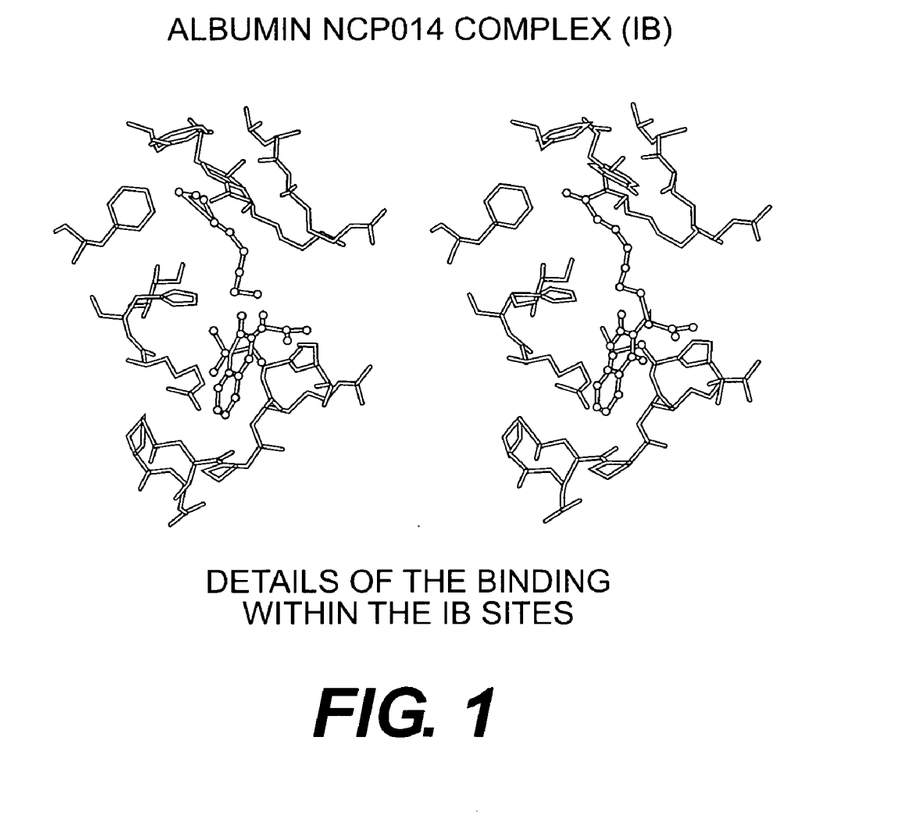
FIG. 1 is a crystallographic view of the albumin binding properties of coumarin analog compound NCP 014 at the binding region IB in accordance with the present invention.
Figure 2:
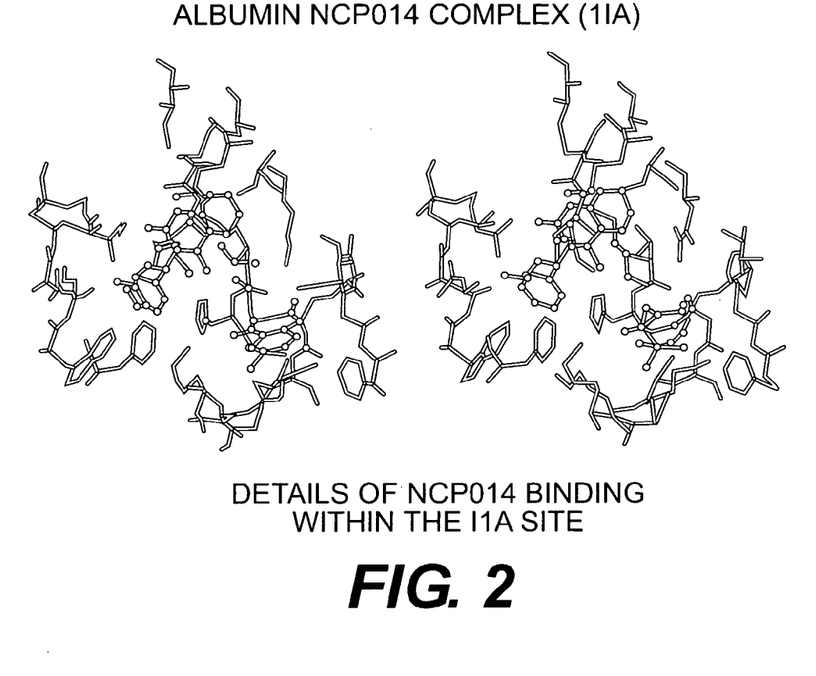
FIG. 2 is a crystallographic view of the albumin binding properties of coumarin analog compound NCP 014 at the binding region IIA in accordance with the present invention.
Figure 3:
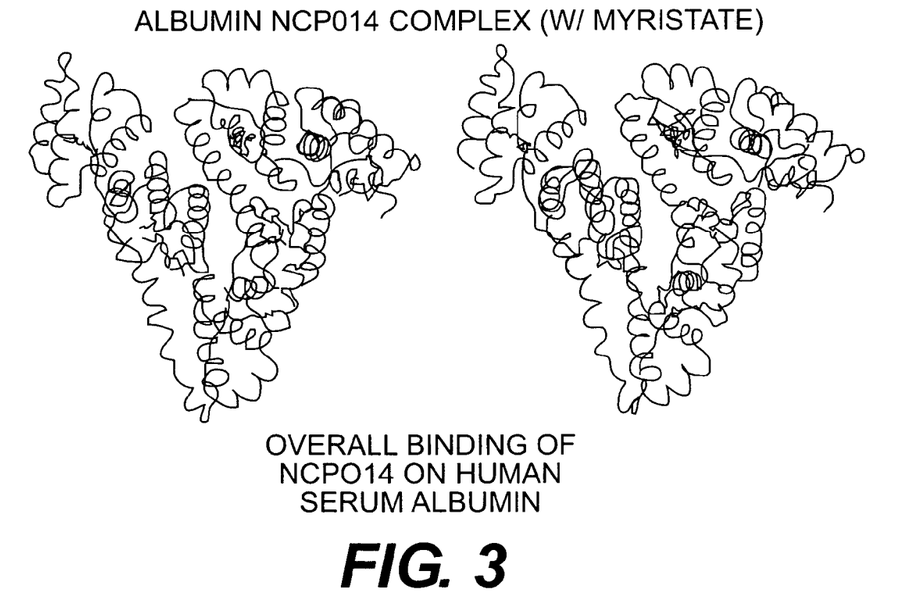
FIG. 3 is a crystallographic view of the overall albumin binding properties of coumarin analog compound NCP 014 in accordance with the present invention.
Figure 4A:
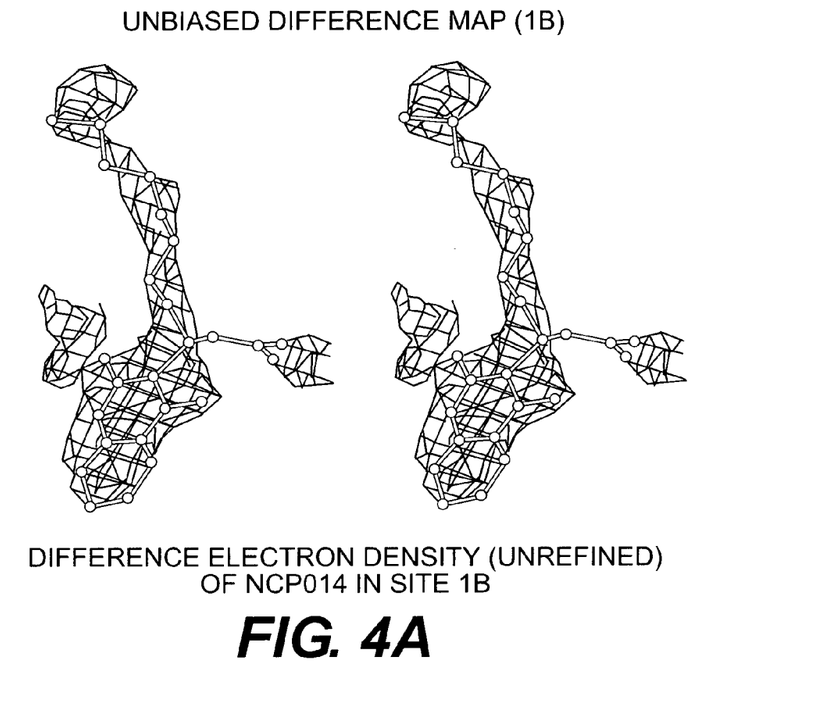
FIG. 4a is a crystallographic view of the difference in electron density (unbiased and unrefined) of the compound NCP014 in accordance with the present invention as bound in site IB of serum albumin.
Figure 4B:
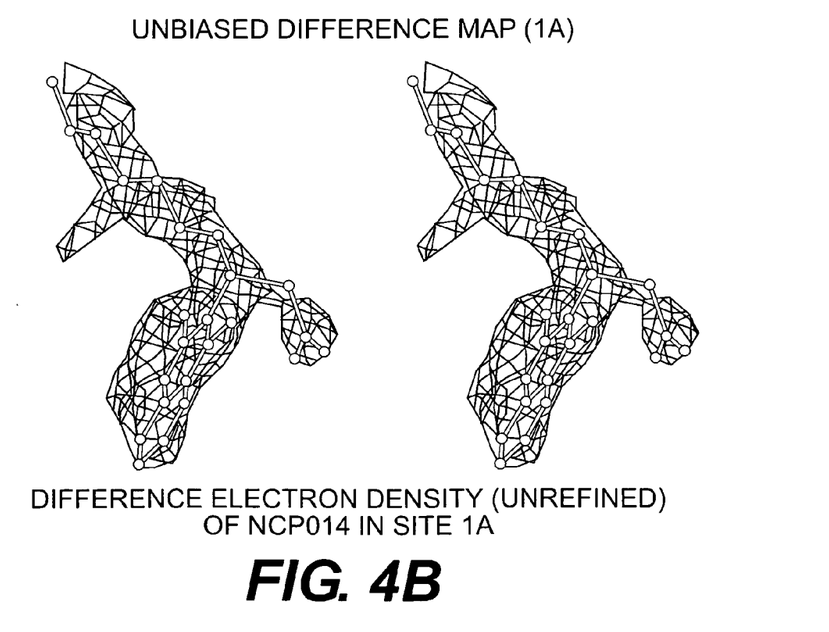
FIG. 4b is a crystallographic view of the difference in electron density (unbiased and unrefined) of the compound NCP014 in accordance with the present invention as bound in site IA of serum albumin.
Figure 5:
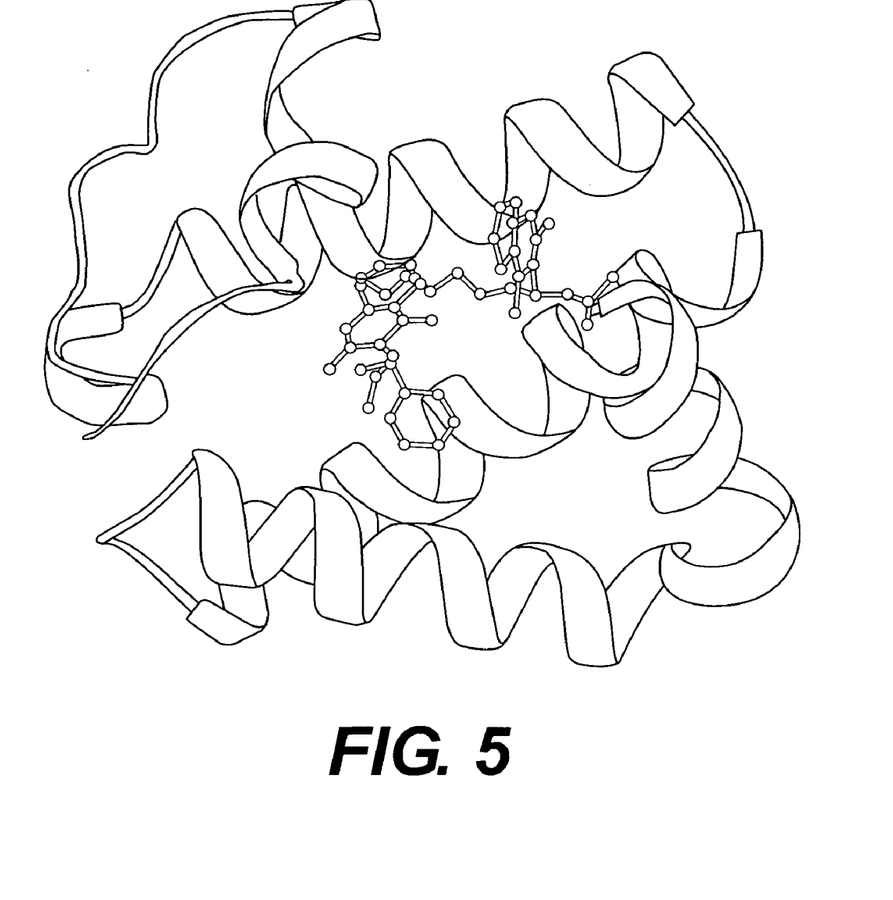
FIG. 5 is a crystallographic view of the binding of the prior art sodium warfarin at its subsite binding region located in region IIA of serum albumin which also shows that the binding of coumarin analog NCP 014 in accordance with the invention binds serum albumin at a separate binding site within the binding region IIA.
Figure 6A:
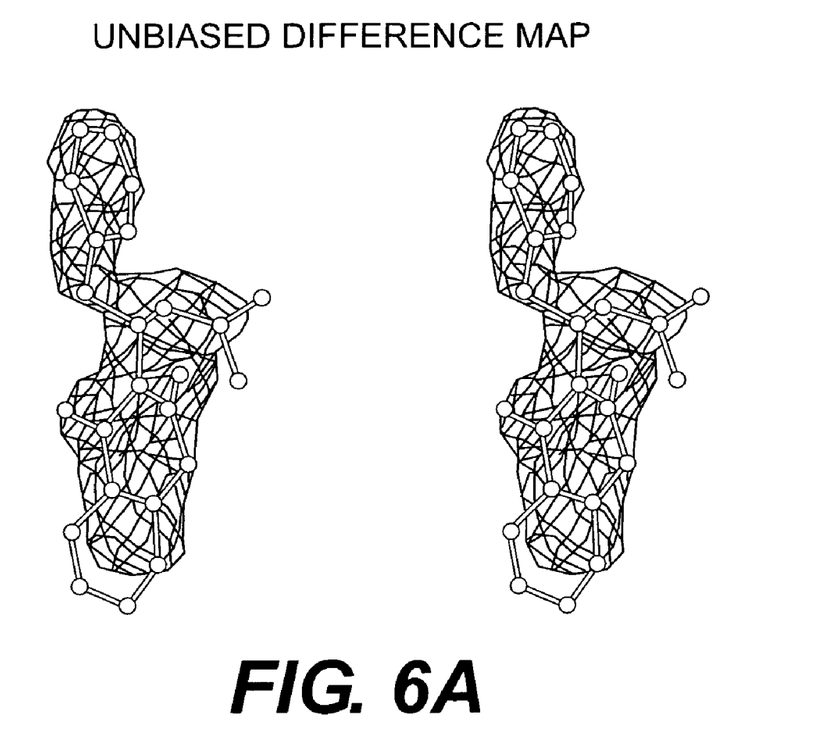
FIG. 6a is a crystallographic view of the difference electron density (unbiased and unrefined) of the compound NCP023 in accordance with the present invention as bound within its unique single site binding location within the albumin binding region known as subdomain IB.
Figure 6B:
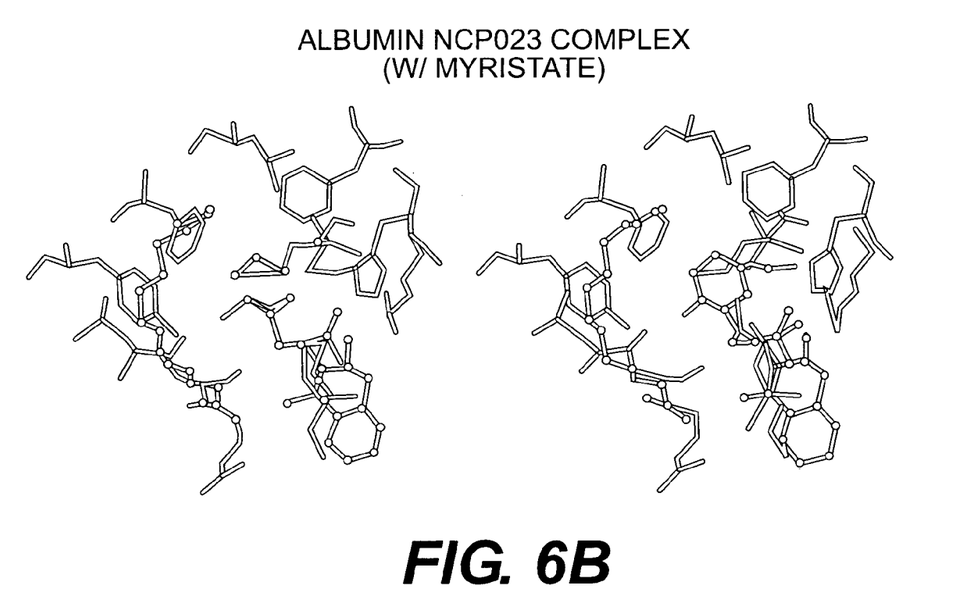
FIG. 6b is a crystallographic view of the atomic interactions of NCP023 within the IB binding location, also shown together with the presence of myristate nearby, but not overlapping with NCP023.

NCP023, NCP023a, and NCP014, among many other coumarin analogs, were examined in accordance with the present invention to determine the nature of the binding of albumin so as to identify and isolate those analogs which will have a binding site different from that of sodium warfarin and which will thus be suitable for use in more stable and safer anticoagulant therapy in accordance with the present invention. Crystallographic information reflecting these analogs is shown in FIGS. 1–3,4a and 4b, 5, and 6a and 6b in accordance with the invention wherein coumarin analogs NCP 014 and NCP023 are shown to bind to binding region IB and/or IIA binding regions of human serum albumin, but at a site which differs from the major, well known site of sodium warfarin in the IIA region. The crystallographic pictures showing the binding of sodium warfarin inside the IIA binding region of serum albumin is shown in FIG. 5. As also shown in FIG. 5, the warfarin/Coumadin® binding site is distinct from the binding location of NCP 014 within the albumin IIA binding region.

The above coumarin analogs in accordance with the present invention will thus be suitable for use in anticoagulant therapy and will provide a more stable reservoir of the anticoagulant drug than in cases wherein analogs such as sodium warfarin are used which are more subject to drug displacement. In the preferred embodiment, the coumarin analog compounds of the present invention will be utilized in composition wherein a suitable and pharmaceutically acceptable vehicle, carrier or excipient is used as would be recognized by one of ordinary skill in this art. The vehicle, excipient or carrier may be any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Generally, the compositions of the present invention are designed for oral administration, but alternative methods of administration when necessary in particular cases include anal, vaginal, intravenous, intraperitoneal, intramuscular, subcutaneous, intranasal and intradermal when oral administration is not feasible.

In addition, the coumarin analog compounds of the invention may be employed in anticoagulant compositions wherein the compounds are included in an amount effective to achieve the desired anticoagulant effect, e.g., the prevention of blood coagulation, in the patient. As indicated above, by "effective amount" is meant that nontoxic but sufficient amount of the anticoagulant agent which will obtain the desired inhibitory, prophylactic or therapeutic effect in the patient in need of anticoagulant therapy. As will be pointed out below, the exact amount of the antibody or a particular agent that is required will vary from subject to subject, depending on the species, age, gender and general condition of the subject, the severity of the condition being treated, the particular carrier or adjuvant being used and its mode of administration, and the like. Accordingly, the "effective amount" of the active agent or compositions containing the active agent will vary based on the particular circumstances, and an appropriate effective amount may be determined in each case of application by one of ordinary skill in the art using only routine experimentation. The dose should be adjusted to suit the individual to whom the composition is administered and will vary with age, gender, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In additional embodiments, the coumarin analogs of the present invention may be utilized in mixtures wherein additional anticoagulant compounds such as sodium warfarin may be used. Such compounds may form a combined treatment regimen wherein the effect of the initial anticoagulant based on sodium warfarin is immediate but not continued long-term, and the effect of the coumarin analog of the present invention, as controlled by its ability to be retained by serum albumin, will give a far longer-lasting anticoagulant effect.

In short, the coumarin analogs of the present invention are advantageous in that they are selected by virtue of their affinity for binding sites on albumin other than the binding site common to sodium warfarin and the other forms of warfarin, a site which also forms the binding site for numerous other drugs and compounds, and compositions made which include these compounds will be advantageous in their effectiveness for anticoagulant therapy without harmful side effects. The coumarin analogs of the present invention will thus bind at sites which have altered affinity for the analog, yet are far less likely to be displaced by other drugs because the alternative sites do not appear to have a large number of competing drugs or compounds that bind at those sites. The coumarin analogs of the present invention can thus provide the same effective anti-coagulant properties of the prior art warfarin compounds but are safer and more effective because of the greater likelihood that the analogs of the invention will remain in a more controlled equilibrium with the serum albumin in the bloodstream and not be released from albumin at undesirable levels due to drug or endogenous ligand displacement interactions.

In another aspect of the present invention, the above described coumarin compounds can be utilized in methods of anti-coagulant therapy wherein an effective amount of the coumarin analog of the present invention is administered to a patient in need of such therapy. As indicated above, by "effective amount" is meant that amount that will be administered to a given human or animal patient so as to achieve an a desired anticoagulant result, e.g., the prevention of blood coagulation when so desired in a patient in need of therapy, and such an amount will be dependent on a variety of factors such as patient gender, size and condition and will thus vary from patient to patient as would be recognized by one of ordinary skill in the art. Accordingly, methods are provided wherein treatment for problems associated with excessive blood coagulation, e.g., stroke and embolism, is accomplished by administering an effective amount of the coumarin analogs of the present invention, or compositions containing said coumarin analogs as described in detail above.

Another aspect of the present invention is thus a method for achieving safe and effective blood coagulation prevention which comprises administering to a patient in need of such therapy an effective amount of a coumarin analog in accordance with the invention as described above, or a pharmaceutical composition containing said coumarin analog as described above.

In summary, the present invention provides a new method of obtaining safer and more effective coumarin analogs which can provide anticoagulant or antithrombotic properties and yet not be subject to drug displacement as would be the case with conventional coumarin analogs such as sodium warfarin which are more likely to be displaced and cause a variety of metabolic and/or medical problems.

It is thus submitted that the foregoing embodiments are only illustrative of the claimed invention and not limiting of the invention in any way, and alternative embodiments that would be obvious to one skilled in the art not specifically set forth above also fall within the scope of the claims.

The following examples are presently only as illustrative of certain aspects of the present invention and do not act to limit the scope of the invention in any way.

EXAMPLES

In the following examples, Biacore and Animal Study data were obtained with regard to some of the compounds of the present invention, namely NCP 014, 023, 023a.

In each case, the studies showed that the particular coumarin analog of the invention bound to albumin at a binding site distinct from that of sodium warfarin.

| NCP | Protein | Binding Sites | $K_{D1}$ µM | $K_{D2}$ µM |
|---|---|---|---|---|
| 014 | HSA | 2 | 0.7 | 130 |
| 014 | HSA | 2 | 0.8 | 110 |
| 014 | HSA | 2 | 4.6 | Not provided |
| 014 | HSA | 1 | 6.5 | N/A |
| 014 | HSA Fragment | 2 | 0.3 | 97 |
| 014 | HSA Fragment | Not determined | Not determined | Not determined |
| 014 | HSA Fragment | 2 | 18.0 | Not provided |
| 014 | HSA Fragment | 1 | 63.0 | N/A |
| 014 | Rat Albumin | 2 | 4.6 | Not provided |

Prothrombin Time (PT) ~52 sec, 24 hrs after 25 mg bolus of NCP 014 delivered orally in water In this case, NCP 014 was observed to bind at the IB binding site, and in addition in the IIA binding site, but at a location different than the major site wherein sodium warfarin binds to albumin.

EXAMPLE 2

BIACORE and Animal Study Data on NCP 023 and 023a

| NCP | Protein | Binding Sites | $K_{D1}$ µM | $K_{D2}$ µM |
|---|---|---|---|---|
| 023 | HSA | 2 | 1.7 | 112 |
| 023 | HSA | 2 | 2.4 | 160 |
| 023 | HSA | 2 | 20.0 | Not provided |
| 023 | HSA | 1 | 103.0 | N/A |
| 023 | HSA Fragment | 2 | 2.7 | 220 |
| 023 | HSA Fragment | 1 | 83.0 | N/A |
| 023 | HSA Fragment | Not determined | Not determined | Not determined |
| 023 | Rat Albumin | | 85.0 | Not provided |
| 023a | HSA | 1 | 23.0 | N/A |
| 023a | HSA | 2 | 0.5 | 40 |
| 023a | HSA | 2 | 12.0 | Not provided |
| 023a | HSA | 1 | 66.8 | N/A |
| 023a | HSA Fragment | 2 | 0.7 | 50 |
| 023a | HSA Fragment | Not determined | Not determined | Not determined |
| 023a | HSA Fragment | 1 | 79.0 | N/A |
| 023a | HSA Fragment | 1 | 122.0 | N/A |
| 023a | Rat Albumin | 2 | 11.8 | Not provided |

Prothrombin Time (PT) ~50 sec, 24 hrs after 25 mg bolus of NCP 023 delivered orally in water
Prothrombin Time (PT) ~61 sec, 24 hrs after 25 mg bolus of NCP 023a delivered orally in water

In these cases, NCP 023 and 023a were observed to bind at a site other than the IIA binding site at which sodium warfarin binds to albumin. In particular, these compounds were determined to bind at the IB site of serum albumin unique from the IB endogenous long-chain fatty acid site.

What is claimed is:

1. A coumarin analog having the formula selected from the group consisting of:

-continued

, and

2. An anticoagulant composition comprising the coumarin analog of claim 1 and a pharmaceutically acceptable vehicle, carrier or excipient.

3. An anticoagulant composition according to claim 2 wherein the coumarin analog is included in an amount effective to inhibit coagulation of the blood in a patient in need of such therapy.

4. The anticoagulant composition according to claim 2 further comprising a second compound having anticoagulant properties.

5. The anticoagulant composition according to claim 4 wherein the second compound having anticoagulant properties is sodium warfarin.

6. A method of inhibiting or preventing blood coagulation in a patient in need of such therapy comprising administering an effective amount of the coumarin analog according to claim 1.

7. A method of preventing blood coagulation in a patient in need of such therapy comprising administering the composition according to claim 2 in an amount effective to achieve inhibition or prevention of blood coagulation.

* * * * *